United States Patent [19]

Tabas

[11] Patent Number: 4,987,151
[45] Date of Patent: Jan. 22, 1991

[54] TRITERPENE DERIVATIVES CHOLESTEROL ACYLTRANSFERASE INHIBITORS AND METHODS OF USING SAME

[75] Inventor: Ira A. Tabas, New City, N.Y.

[73] Assignee: The Trustees of Columbia University in the City of New York, New York, N.Y.

[21] Appl. No.: 367,900

[22] Filed: Jun. 19, 1989

[51] Int. Cl.$^5$ .................. C07C 229/00; C07C 62/00; A61K 31/215; A61K 31/19

[52] U.S. Cl. .................................. 514/548; 514/559; 560/173; 562/508

[58] Field of Search ................ 514/548, 559; 560/173; 562/508; 435/184

[56] References Cited

U.S. PATENT DOCUMENTS 4,448,788  5/1984  Toyoshima et al. ................ 514/548

FOREIGN PATENT DOCUMENTS 1112089  5/1986  Japan .................................. 435/184

OTHER PUBLICATIONS

A. S. Katocs, et al., (1988), *The Faseb Journal*, 2:A1219 (Exhibit 2).
L. L. Gallo, et al., (1987), *J. Lipid Res.*; 28:381 (Exhibit 3).
B. Middleton et al., (1987), *Drugs*, 33 (Sup. 2): 75–79 (Exhibit 4).
J. L. Kelly et al., (1988), *Biochimica Et Biophysica Acta*, 960:83–90 (Exhibit 5).
E. E. Largis, et al., (1989), *J. Lipid Res.*; 30:681–690 (Exhibit 6).
S. B. Clark et al., (1984), *J. Lipid Res.*; 25:148–159 (Exhibit 7).
J. G. Heider et al., (1983), *J. Lipid Res.*; 24:1127–34 (Exhibit 8).
S. A. Schaffer, et al., (1986), *Atherosclerosis VII*; 633–636 (Exhibit 9).
I. Tabas et al., (1986), *J. Biol. Chem.*; 261:3147–3155 (Exhibit 10).

Nozakli et al. J. Chem Soc. Chem Commun. 1982 pp. 1048–1051.

*Primary Examiner*—Mukund J. Shah
*Assistant Examiner*—E. C. Ward
*Attorney, Agent, or Firm*—John P. White; Robert D. Katz

[57] ABSTRACT

The present invention provides a purified compound of the structure;

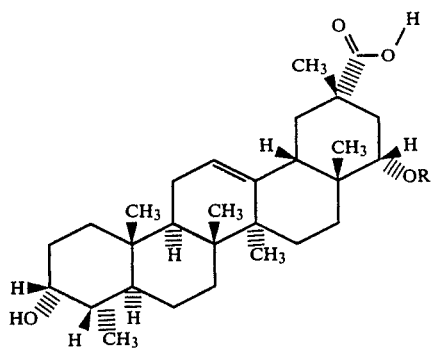

wherein R may be palmitoyl or steroyl. The invention also provides compositions comprising an admixture of the foregoing palmitate and stearate esters.

The invention also provides a compound of the structure:

(Abstract continued on next page.)

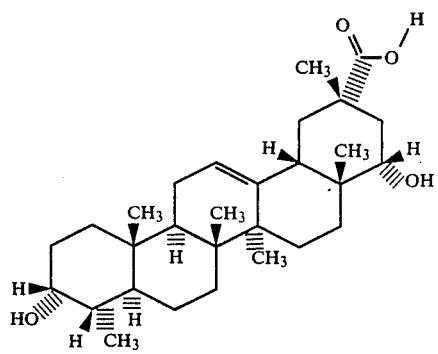
The invention further provides pharmaceutical compositions including the aforementioned compounds and compositions and methods of inhibiting the acyl CoA: cholesterol acyltransferase catalyzed conversion of cholesterol to cholesteryl esters.
24 Claims, 5 Drawing Sheets

TRITERPENE DERIVATIVES CHOLESTEROL ACYLTRANSFERASE INHIBITORS AND METHODS OF USING SAME

BACKGROUND OF THE INVENTION

Acyl-CoA: cholesterol acyltransferase (ACAT) is an intracellular enzyme found in several different sites in the body, including the intestinal tract and the liver, which catalyzes the esterification of fatty acid and cholesterol to form cholesteryl esters. Cholesteryl esters, unlike cholesterol, may be absorbed from the intestinal tract into the bloodstream, and are found in cholesteryl ester laden "foam cells" contained in atherosclerotic lesions. Thus inhibition of ACAT may, by preventing cholesterol absorption from the intestinal tract into the bloodstream, help reverse, retard or prevent the atherosclerotic process. ACAT inhibition using a tryptophan ester derivative compound identified as Sandoz Compound 57-118 has been demonstrated to prevent cholesterol absorption in cholesterol fed rabbits (Heider, et al., "Role Of Acyl CoA:Cholesterol Acyltransferase In Cholesterol Absorption And Its Inhibition By 57-118 In The Rabbit", *J. Lipid Res.*, Vol. 24, pp. 1127–34 (1983)).

Another series of experiments involving Lederle Compound CL 277,082, a trisubstituted urea compound, demonstrated that ACAT inhibition could play a role in decreasing cholesterol concentrations in plasma, liver, and aorta in rats (Schaffer, et al., "CL 277,082, A Novel Inhibitor Of Cholesterol Esterification And Cholesterol Absorption", Atherosclerosis VII, Fidge and Nestel, eds., pp. 633–36 (1986)), while a different series of experiments, involving Sandoz Compound 58-035, demonstrated that ACAT inhibition can help prevent foam cell formation in tissue culture macrophages (Tabas, et al., "Inhibition of Acyl Coenzyme A:Cholesterol Acyl Transferase in J774 Macrophages", *J. Biol. Chem.*, Vol., 261, pp. 3147–55 (1986)). The disclosures of foregoing publications in their entireties are hereby incorporated by reference into this application in order to more fully describe the state of the art as known to those skilled therein as of the date of the invention described and claimed.

The foregoing compounds, however, are all synthetic compounds, and in animal or early human trials apparently have demonstrated undesirable side effects of toxicities.

SUMMARY OF THE INVENTION

This invention provides a purified compound having the structure:

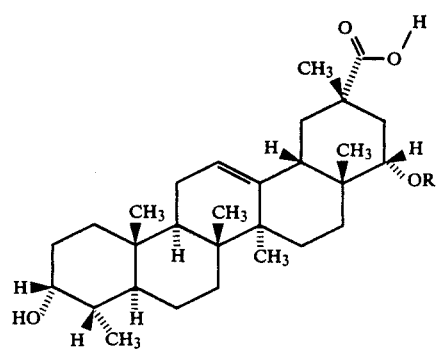

wherein R may be palmitoyl (C(O)C$_{15}$H$_{31}$) or steroyl (C(O)C$_{17}$H$_{35}$).

This invention also provides a compound having the structure:

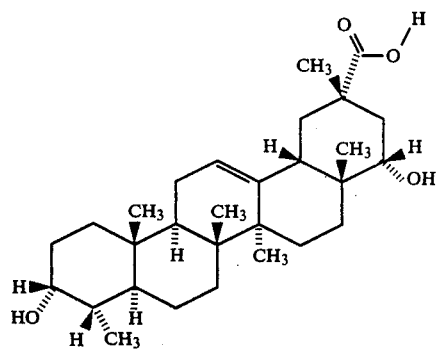

This invention further provides a purified composition comprising an admixture of a compound having the structure

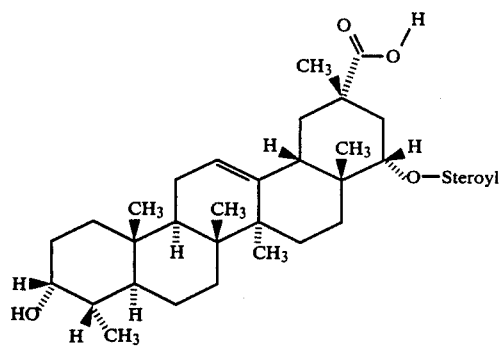

and a compound having the structure

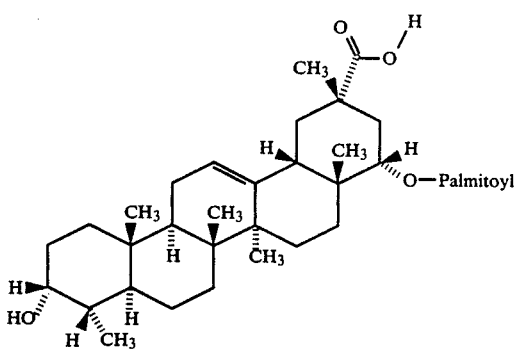

wherein the molar ratio of the stearate ester to the palmitate ester is about 4:1.

The invention additionally provides a pharmaceutical composition comprising an amount of one or more of the foregoing compounds or compositions effective to inhibit the acyl coenzyme A: cholesterol acyltransferase catalyzed esterification of cholesterol in a mammal and a pharmaceutically acceptable carrier.

This invention further provides a method of inhibiting acyl coenzyme A: cholesterol acyltransferase catalyzed esterification of cholesterol which comprises contacting the acyl coenzyme A: cholesterol acyltransferase with an effective inhibiting amount of one or more of the novel compositions or compounds disclosed above.

This invention additionally provides a method for inhibiting the acyl coenzyme A: cholesterol acyltransferase-catalyzed esterification of cholesterol in a mammal comprising administering to the mammal an amount of one or more of the compounds or compositions disclosed herein.

DETAILED DESCRIPTION OF THE INVENTION

Figure 1:
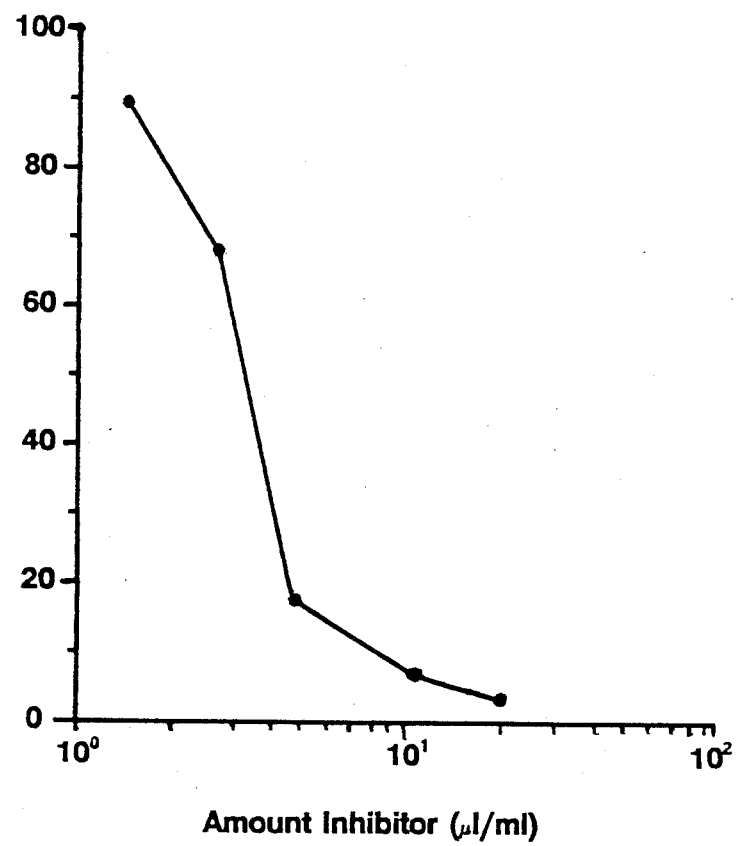
FIG. 1 is a graph depicting inhibition of Rat Liver Microsomal ACAT Activity by the Purified Composition of the Present Invention Wherein a Mixture of the Stearate Ester and Palmitate Ester in an Approximately 4:1 Ratio Is Assayed.

This invention provides a purified compound having the structure:

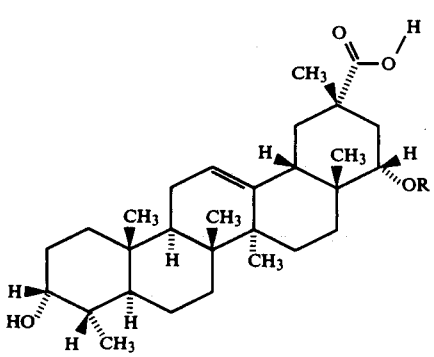

wherein R may be palmitoyl (C(O)C$_{15}$H$_{31}$) or steroyl (C(O)C$_{17}$H$_{35}$). These esters preferably are isolated and purified from rabbit liver, and may be used in admixture or may include only the steroyl (C(O)C$_{17}$H$_{35}$) or palmitoyl (C(O)C$_{15}$H$_{31}$).

This invention also provides a compound having the structure:

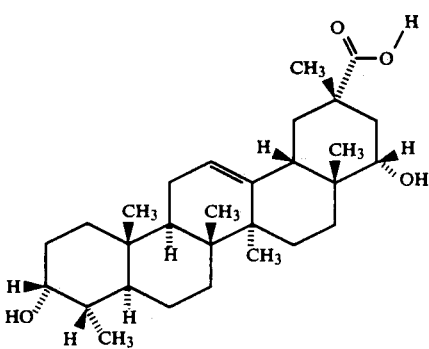

This compound may preferably be obtained by hydrolyzing either the palmitate or stearate esters disclosed above.

This invention further provides a purified composition comprising an admixture of a compound having the structure:

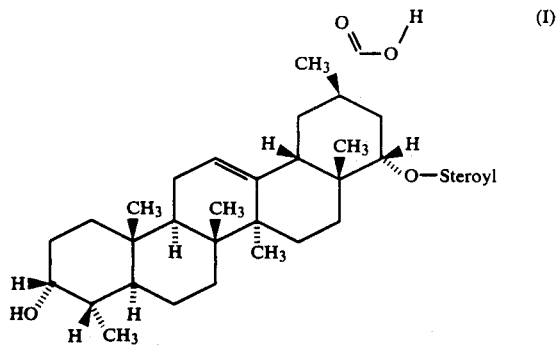

and a compound having the structure:

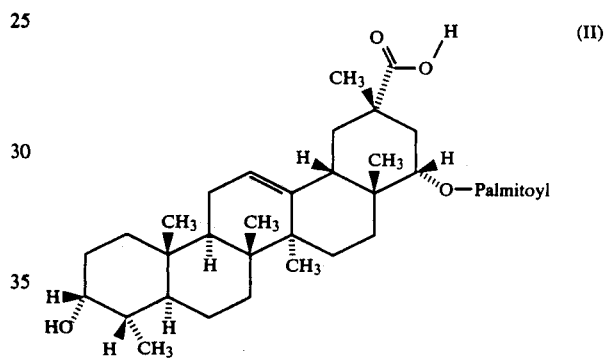

wherein the molar ratio of I to II is between about 5:1 and about 1:5, although a composition wherein the molar ratio of I to II is about 4:1 seems preferred.

Additionally, although a particular stereoisomer of the compounds and compositions of the present invention is illustrated herein using the convention of dashed and solid lines, other effective stereoisomers are included in the scope of the present invention.

This invention also provides a pharmaceutical composition which comprises an amount of one or more of the purified stearate or palmitate esters of the free hydroxyl compound effective to inhibit the acyl coenzyme A: cholesterol acyltransferase-catalyzed esterification of cholesterol in a mammal and a compatible pharmaceutically acceptable carrier. Such pharmaceutical compositions may also include an amount of an admixture of the stearate and palmitate esters (where the molar ratio of the stearate ester to the palmitate ester is from about 5:1 to about 1:5) effective to inhibit the ACAT catalyzed esterification of cholesterol in a mammal and a pharmaceutically acceptable carrier.

As used herein, the term "pharmaceutically acceptable carrier" encompasses any of the standard pharmaceutical carrier such as a phosphate buffered saline solution, water, emulsions such as oil/water emulsion, and various types of wetting agents.

In this method, the administration of the compound may be effected by any of the well known methods, including but not limited to intravenous, intramuscular, and subcutaneous administration.

The compounds and compositions of the present invention may also be administered orally in tablets or capsules. If the compositions and compounds are included in the tablets, they can be mixed with any of the standard tableting agents, lubricants and excipients, such as dextrose, talc, cellulose, lactose, silicas and corn starch. Such a tablet may also include a sugar or film coating to protect the compositions from moisture, oxygen or light or an enteric coating, or they may be compounded to provide sustained release of the compounds and the compositions by microencapsulation or other standard techniques.

The term "effective amount" as used herein is an amount sufficient to inhibit the ACAT enzyme from esterifying cholesterol and fatty acids to cholesteryl esters. The actual amount used varies depending on which compound or composition or admixture is used. For example, the free hydroxyl compound seems to have less activity than an admixture of the stearate and palmitate esters. The actual dosages may vary from about 0.1 mg/kg/day to about 50 mg/kg/day, and may be adjusted by a person of ordinary skill in the art to maximize effectiveness while avoiding side effects and toxicities.

This invention also provides a method of inhibiting acyl coenzyme A: cholesterol acyltransferase-catalyzed esterification of cholesterol which comprises contacting the acyl coenzyme A: cholesterol acyltransferase with an effective inhibitory amount of the compound of the aforementioned purified stearate or palmitate ester compounds of the aforementioned free hydroxyl compound.

This invention further provides a method of inhibiting acryl coenzyme A: cholesterol acyltransferase-catalyzed esterification of cholesterol which comprises contacting the acyl coenzyme A: cholesterol acyltransferase with an effective inhibitory amount of the aforementioned purified admixture of the stearate and palmitate esters, wherein the molar ratio of the stearate to palmitate esters is between about 5:1 and about 1:5, and preferably is 4:1.

This invention additionally provides a method for inhibiting the acyl coenzyme A: cholesterol acyltransferase-catalyzed esterification of cholesterol in a mammal comprising administering to the mammal an amount of the aforementioned purified stearate and palmitate ester compounds or the free hydroxyl compound and a compatible pharmaceutically acceptable carrier.

This invention also provides a method for inhibiting the acyl coenzyme A: cholesterol acyltransferase-catalyzed esterification of cholesterol in a mammal comprising administering to the mammal an amount of a composition which is an admixture of the aforementioned purified palmitate and stearate esters, wherein the molar ratio of stearate to palmitate ester is between about 5:1 to about 1:5 and a compatible pharmaceutically acceptable carrier, although a molar ratio of about 4:1 of stearate to palmitate ester is presently preferred.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

I. Extraction of Lipid 100 g of fresh or frozen rabbit liver (which had been previously thawed) was chopped into approximately 2 mm pieces and washed several times with distilled $H_2O$. The water was drained, and to the liver pieces were added 30 ml of chloroform/methanol (1:2, v/v) containing 1 ug/ml butylated hydroxytoluene.

The material was homogenized for 2 minutes in a Waring blender at room temperature and centrifuged for 10 minutes at 1,000 rpm at 10° C. (IEC Model CRU 5000 centrifuge) in 250 ml glass centrifuge bottles (Belco). The supernate was collected and the liver residue was reextracted with 380 ml of chloroform/methanol/distilled $H_2O$ (1:2:0.8, v/v). The supernates were pooled. 140 ml of chloroform and 140 ml of distilled $H_2O$ was added to the combined supernates. The material was mixed well by shaking and then centrifuged for 10 minutes at 1,000 rpm (10° C.) to separate into two phases. When a milky middle phase appeared the clear top phase was removed and discarded. 20 ml of methanol was added to the middle/bottom phase, and the mixture was centrifuged again. The clear bottom (organic) phase was collected into a 500 ml round bottom flask, 1 ml of benzene was added, and the solvent was removed under vacuum by rotary evaporation. The dry weight of lipid was recorded. The dried residue was resuspended in 10 ml hexanes/diethyl ether (1:1, v/v) and filtered through glasswool.

II. Separation with Unisil Silicic Acid Column 18 g of Unisil silicic acid (100–200 mesh; Clarkson Chemicals, Williamsport, Pa.) was heated at 120° C. for 1 hour. The silicic acid was mixed with hexanes/diethyl ether (1:1, v/v) to form a slurry, poured into a 17×300 mm glass column plugged with glasswool, and washed with 100 ml of hexanes/diethyl ether (1:1, v/v). (All column work was performed at room temperature.)

The lipid extract was loaded onto the silicic acid column. The column was washed with 200 ml of hexanes/diethyl ester (1:1, v/v) and this fraction was discarded. The lipids of interest were eluted with 200 ml of diethyl ether/methanol (7:3, v/v/). The solvent was removed from this fraction by rotary evaporation.

6 ml of methanol was added to the dried lipid fraction, and the mixture was warmed to 37° C. and agitated by swirling for 5 minutes. The methanol-soluble material was colleted and passed through glasswool. The material was evaporated under nitrogen and resuspended in 1 ml of chloroform.

III. Purification with Thin Layer Chromotography

Two 20×20 cm preparative TLC plates (Adsorbosil-plus 1 [500 um], Alltech Associates, Deerfield, Ill.) were heated at 100° C. for 30 minutes. The chloroform-dissolved sample was applied to the two TLC plates (0.5 ml per plate) and developed four times in succession in n-heptane/isopropyl ether/glacial acetic acid (60:4-:4, v/v).

Upon exposure to iodine vapor, a broad band of staining appeared extending from the origin to approximately 6 cm above the origin. The material of interest migrated in a band (not usually visualized by iodine staining) whose bottom and top edges were approximately 1 cm and 3 cm, respectively, above the top edge of the broad iodine-stained bottom band. The band of interest as well as 1 cm bands above and below it were scraped separately into 40 cc glass conical tubes. A narrow vertical strip at one of the edges of the TLC plate was left for definitive band identification by the $H_2SO_4$/charring method (sprayed with 50% $H_2SO_4$ and then the plate charred on a heating block). The band containing the ACAT inhibitor appeared as a lavender spot which eventually turned black upon further heating.

The collected silica corresponding to the ACAT inhibitor band was then extracted with 22.4 ml of chloroform/methanol/distilled $H_2O$ (1:2:0.8, v/v) by vortexing for 2 minutes. The material was centrifuged for 5 minutes at 1,000 rpm (10° C.) and the supernate was saved. The silica was reextracted with 22.4 ml of chloroform/methanol/distilled $H_2O$ (1:2:0.8, v/v) as described above, and the supernates were combined. 12 ml of chloroform and 12 ml of distilled $H_2O$ were added to the combined supernates and, after mixing well by shaking, were centrifuged for 5 minutes at 1,000 rpm (10° C.). The bottom organic phase was collected and evaporated to dryness under a stream of nitrogen. The residue was dissolved in 2 ml of chloroform and filtered through a glass membrane (#25, Schleicher & Schuell, Keene, N.H.). At this point the chloroform may be evaporated under nitrogen and the dry weight may be measured. The purified inhibitor can be stored in chloroform under argon at −20° C. for up to 3 months without apparent loss of activity. For use in microsomal ACAT experiments, aliquots are evaporated to dryness and resuspended in methanol.

IV. Initial Characterization of the Rabbit Liver ACAT Inhibitor

Processing of 50 grams of rabbit liver according to the procedure outlined above yielded, on the average, approximately 1 mg of homogeneously purified lipid ACAT inhibitor. All of the more than 100 rabbit livers extracted (some freshly harvested from rabbits and some obtained commercially in frozen form) have shown the presence of the inhibitor.

To assay the activity of the purified lipid, 0.9 mg was dissolved in 1 ml methanol and various amounts were assayed according to the following standard microsomal ACAT assay: in 0.1 ml of 0.1M phosphate buffer, pH 7.4, 60 μg of rat liver microsomes were preincubated for 15 minutes at 37° C. with 1 mM cholesterol (dissolved in 4 μL acetone) plus either 4 μl methanol (the original 0.95 mg/ml was either diluted or concentrated so that each of the different concentrations used was added to the assay in a volume of 4 μL). After the 15 minute preincubation, 0.1 ml of phosphate buffer containing 100 uM bovine serum albumin and 100 μM [$^3$H]oleoyl-CoA was added to the mixture, which was then incubated for another 15 minutes at 37° C. The lipids were then extracted and subjected to thin layer chromatography; the cholesterol ester spot was identified, scraped, and counted to determine the amount of the ACAT product—cholesteryl [$^3$H]oleate—formed in the reaction. The data in FIG. 1 show how increasing amounts of the lipid from the 1-ml methanol solution inhibit ACAT activity. Half maximal inhibition occurred at 3 μL, which corresponds to 20 μM. Similar activity occurred when the inhibitor was dissolved in dimethyl sulfoxide instead of methanol. FIG. 1 shows the inhibition of rat liver microsomal ACAT activity by the purified rabbit liver lipid.

Figure 2:
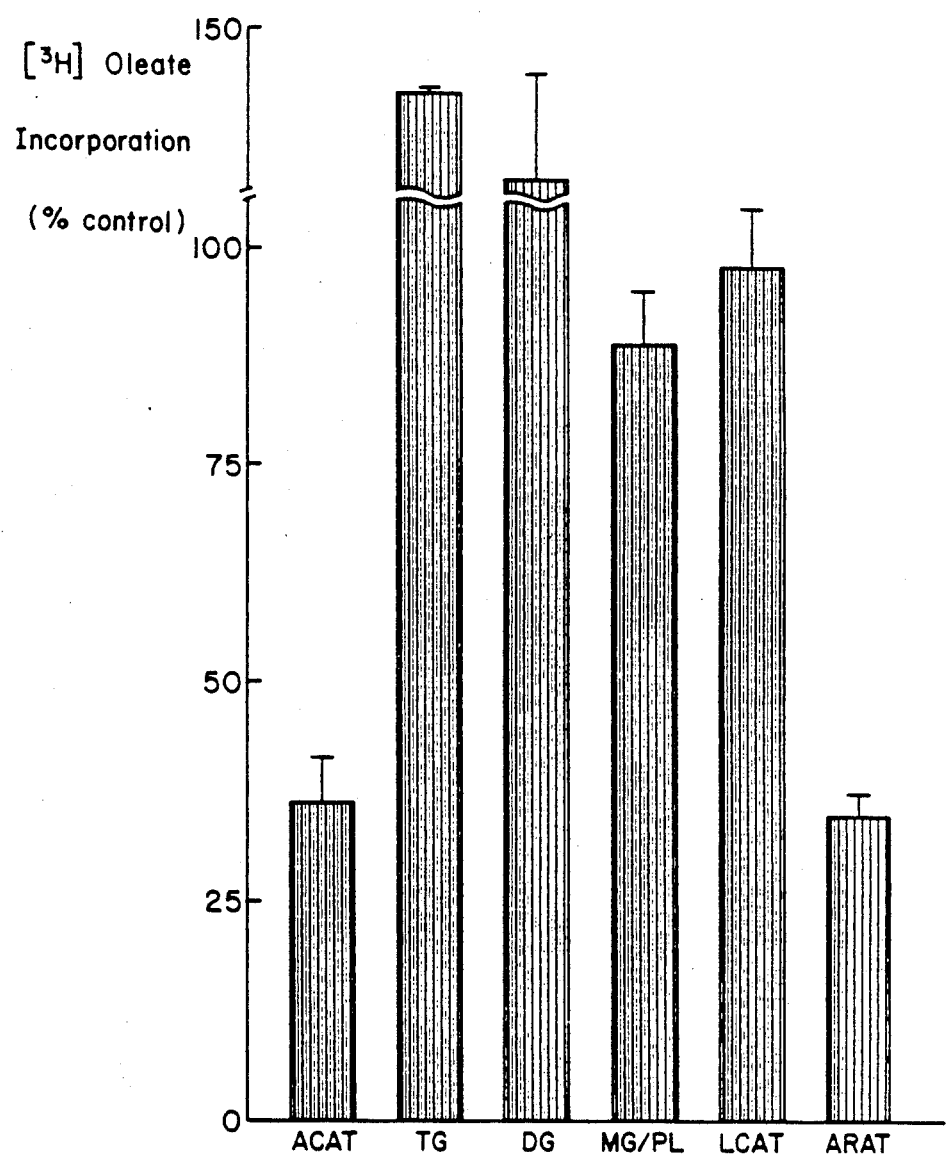
FIG. 2 is a graph depicting the specificity of the Purified Composition of FIG. 1 is determined by assaying its ability to inhibit enzymes other than ACAT.

FIG. 2 shows the specificity of the purified lipid. In this experiment 30 μM lipid was added to various assays as indicated. The lipid inhibited both ACAT and retinol esterification (ARAT) but did not inhibit oleate incorporation into triglyceride (TG), diglyceride (DG), or monoglyceride/phosphlipid (MG/PL)). In addition, the lipid did not inhibit cholesterol esterification catalyzed by the enzyme lethicin:cholesterol acyltransferase (LCAT).

Figure 3:
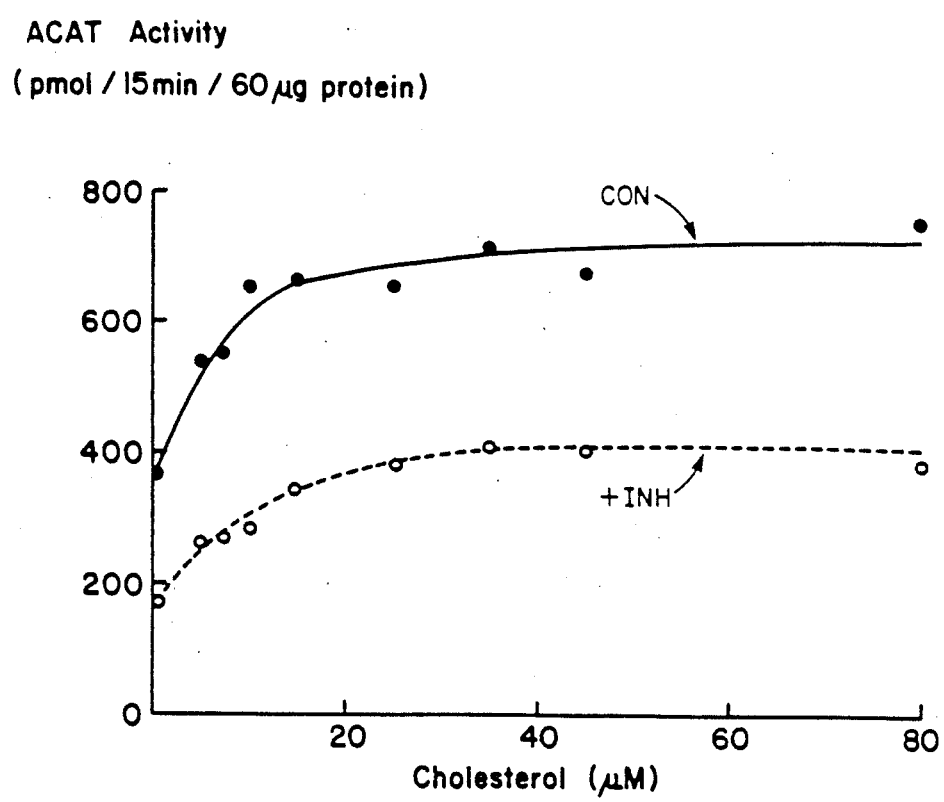
FIG. 3 is a graph which suggests that the Purified Composition of FIG. 1 is not a competitive inhibitor of ACAT.
Figure 3:
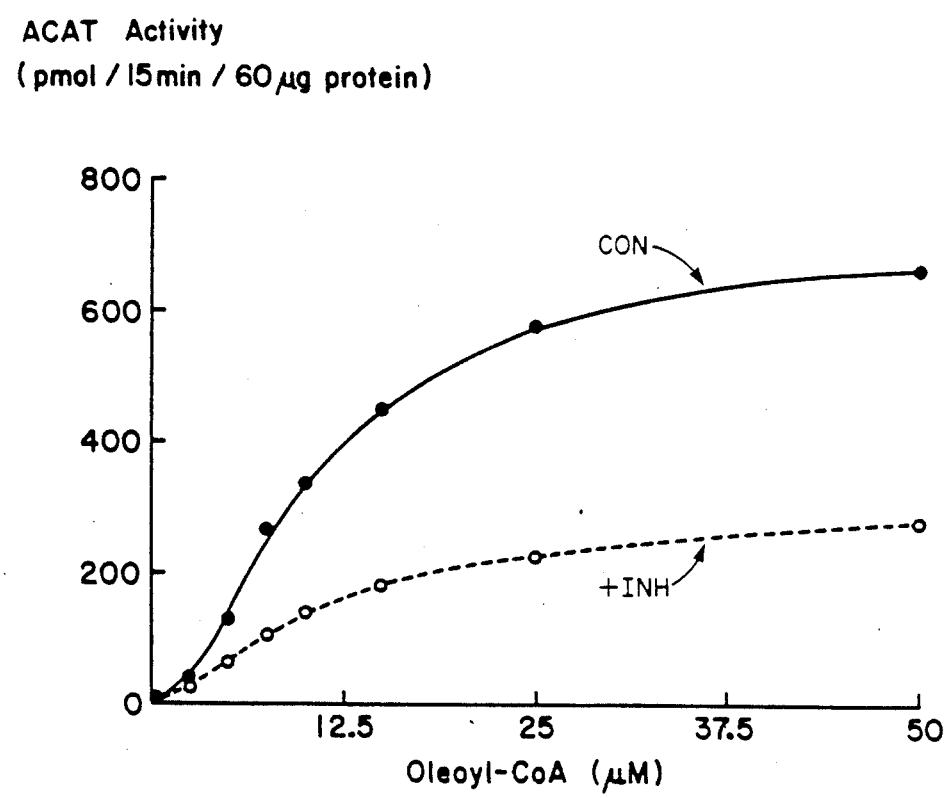

FIG. 3 shows the effect of increasing amounts of the substrates cholesterol (top panel) and oleoyl-CoA (bottom panel) on the activity of ACAT in the absence (solid circles) on in the presence (open circles) of the inhibitor. The data indicate that the inhibitor is not competitive for either substrate, and more detailed analysis of the data suggests noncompetitive-type inhibition.

Figure 4:
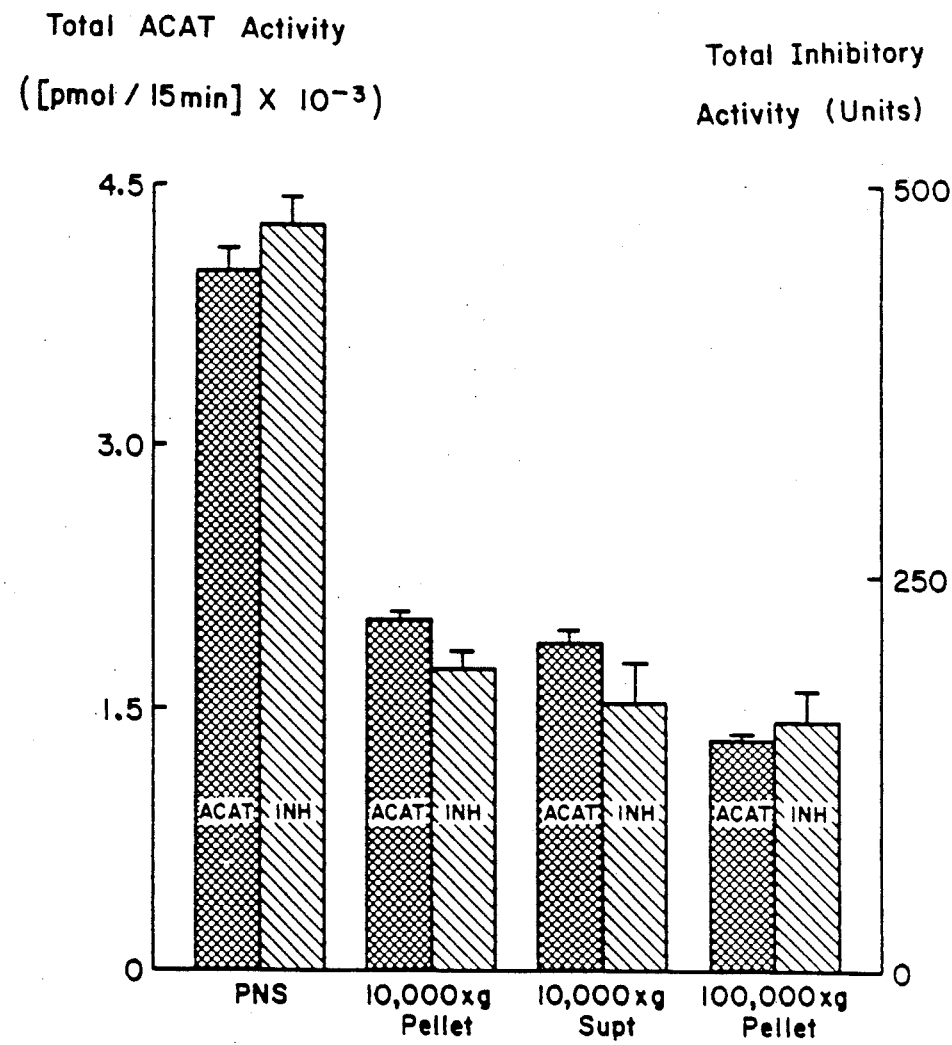
FIG. 4 is a graph containing data on the subcellular distribution of ACAT and the inhibitor in rabbit liver.

FIG. 4 examines the subcellular distribution of ACAT and the inhibitor in rabbit liver. For each subcellular fraction, ACAT activity was measured according to standard means (above) and inhibitory activity was measured as follows: from each fraction, inhibitor was purified by the method outlined above. Various amounts of the purified material were then tested in the ACAT assay, and an inhibitory curve was constructed similar to that in FIG. 1. The amount of inhibitor needed to cause 50% inhibition was defined as one unit, and then the total number of units per fraction was calculated. The data show that the inhibitor is membrane-bound and has a similar distribution as ACAT.

Another experiment was performed in which various tissues were lipid extracted and subjected to Unisil chromatography as described above. The 70:30 (ether:-methanol v/v) fraction was subjected to the TLC system described above. The TLC plate was developed by charring and examined for the presence of a spot corresponding to the inhibitor. The inhibitor was found in multiple organs (e.g. adrenal and spleen) and was also in the plasma. Stool, however, did not have the inhibitor. In addition, antibiotic sterilization of rabbits did not cause the inhibitor in liver to disappear. Thus, it is unlikely that bacteria in the rabbit gut synthesize the lipid, which would then be recirculated back to the liver.

V. Structural Determination of the ACAT Inhibitor

To 25.4 mg (35 μmol) of 1 (see below) was added 1.5 mL 10% aqueous KOH and 1.5 mL of ethanol. The mixture was heated at 45° C. for 20 h, cooled, and the pH was adjusted to ~4 with 1N aqueous HCl. The mixture was extracted with two 25 mL portions of dichloromethane. The combined organic layers were dried (MgSO$_4$) and concentrated in vacuo. The residue was dissolved in 3 mL diethyl ether and treated with an excess of a freshly distilled ethereal solution of diazomethane at 0° C. After 30 minutes, the excess diazomethane was quenched with acetic acid. The solvents were removed in vacuo and the residue was purified by preparative silica gel thin layer chromatography eluting with diethyl ether to give 7 mg (67%) of methyl stearate as an oil ($R_f$=0.85); 7 mg(27%) of 2a ($R_f$=0.76) as a waxy solid identified as the methyl ester 2a; and 9 mg (54%) of the diol methyl ester 2b as a waxy white solid ($R_4$-0.42).

To 6.5 mg (13.7 μmol) of diol 2b in 0.25 mL of dichloromethane was added 7.7 mg (34 μmol) or p-bromobenzoyl chloride and 3.2 mL (40 μmol) pyridine. The mixture was stirred at ambient temperature for 1.5 h. The mixture was partitioned between 15 mL of ethyl acetate and 15 mL of 1N aqueous Hcl. The organic layer was washed with 15 mL 1N aqueous NaOH, dried (Na₂SO₄) and concentrated in vacuo. The residue was purified via preparative silica gel thin layer chromatography eluting with 30% ethyl acetate in hexanes to give 10.5 mg (90%) of the desired bis-bromobenzoate 3 as a white crystalline solid (R$_f$=0.62). This material was recrystallized from ether-hexanes (1:1) to give fine colorless needles suitable for X-ray crystallographic analysis.

From nuclear magnetic resonance and mass spectroscopy of 1 and X-ray crystallography of 3, the structure of 1 was determined.

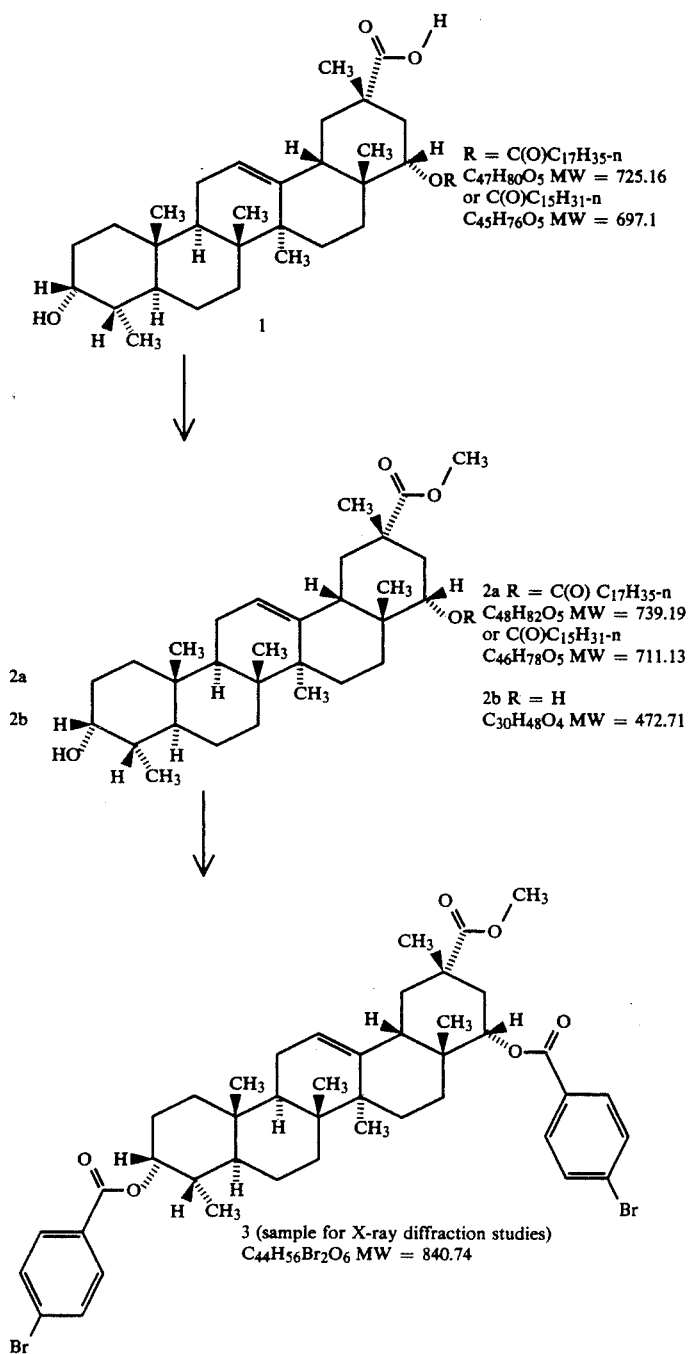

What is claimed is:
1. A purified compound having the structure:

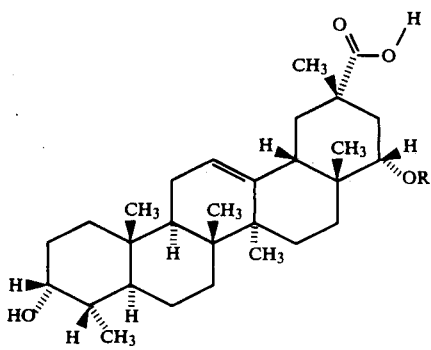

wherein R may be palmitoyl or steroyl.

2. A compound having the structure:

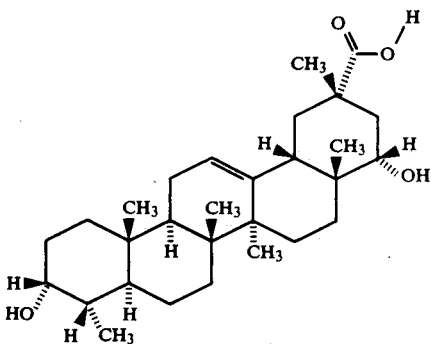

3. A compound of claim 1, wherein R is palmitoyl (C(O)C$_{15}$H$_{31}$).

4. A compound of claim 1, wherein R is steroyl (C(O)C$_{17}$H$_{35}$).

5. A purified composition comprising an admixture of a compound having the structure:

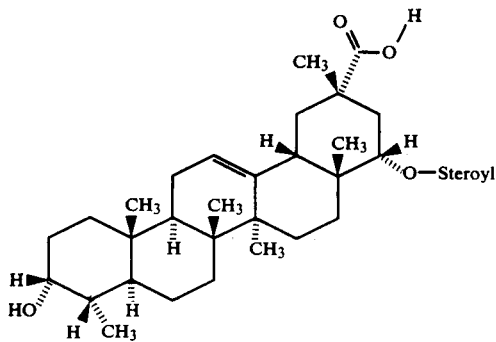

and a compound having the structure:

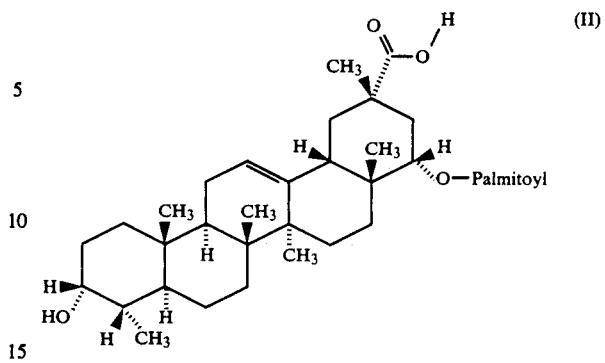

wherein the molar ratio of I to II is between about 5:1 and about 1:5.

6. A composition of claim 5 wherein the molar ratio of I to II is about 4:1.

7. A pharmaceutical composition which comprises an amount of a compound of claim 1 effective to inhibit the acyl coenzyme A: cholesterol acyltransferase-catalyzed esterification of cholesterol in a mammal and a compatible pharmaceutically acceptable carrier.

8. A compound according to claim 7 wherein the effective amount of the compound effective to inhibit the acyl coenzyme A: cholesterol acyltransferase-catalyzed esterification of cholesterol in a mammal is between about 0.1 mg/kg/day and about 50 mg/kg/day.

9. A pharmaceutial composition which comprises an amount of a compound of claim 2 effective to inhibit the acyl coenzyme A: cholesterol acyltransferase-catalyzed esterification of cholesterol in a mammal and a compatible pharmaceutically acceptable carrier.

10. A compound according to claim 9 wherein the amount of the compound effective to inhibit the acyl coenzyme A; Cholesterol acyltransferase catalyzed esterification of cholesterol in a mammal is between about 0.1 mg/kg/day and about 50 mg/kg/day.

11. A pharmaceutical composition which comprises an amount of a composition of claim 5 effective to inhibit the acyl coenzyme A; cholesterol acyltransferase-catalyzed esterification of cholesterol in a mammal and a pharmaceutically acceptable carrier.

12. A composition according to claim 11 wherein the amount effective to inhibit the acyl coenzyme A; cholesterol acyltransferase-catalyzed esterification of cholesterol in a mammal is between about 0.1 mg/kg/day and about 50 mg/kg/day.

13. A method of inhibiting acyl coenzyme A: cholesterol acyltransferase-catalyzed esterification of cholesterol which comprises contacting the acyl coenzyme A: cholesterol acyltransferase with an effective inhibitory amount of the compound of claim 1.

14. A method of inhibiting acyl coenzyme A: cholesterol acyltransferase-catalyzed esterification of cholesterol which comprises contacting the acyl coenzyme A: cholesterol acyltransferase with an effective inhibitory amount of the compound of claim 2.

15. A method of inhibiting acyl coenzyme A: cholesterol acyltransferase-catalyzed esterification of cholesterol which comprises contacting the acyl coenzyme A: cholesterol acyltransferase with an effective inhibitory amount of the composition of claim 5.

16. A method of inhibiting acyl coenzyme A: cholesterol acyltransferase-catalyzed esterification of cholesterol which comprises contacting the acyl coenzyme A:

cholesterol acyltransferase with an effective inhibitory amount of the composition of claim 6.

17. A method of inhibiting acyl coenzyme A: cholesterol acyltransferase-catalyzed esterification of cholesterol in a mammal comprising administering to the mammal an effective inhibitory amount of a compound of claim 1 and a compatible pharmaceutically acceptable carrier.

18. A method in accordance with claim 17 wherein the effective inhibitory amount is between about 0.1 mg/kg/day and about 50 mg/kg/day.

19. A method of inhibiting acyl coenzyme A: cholesterol acyltransferase-catalyzed esterification of cholesterol in a mammal comprising administering to the mammal an effective amount of a compound of claim 2 and a compatible pharmaceutically acceptable carrier.

20. A method in accordance with claim 19 wherein the effective amount is between about 0.1 mg/kg/day and about 50 mg/kg/day.

21. A method for inhibiting the acyl coenzyme A: cholesterol acyltransferase-catalyzed esterification of cholesterol in a mammal comprising administering to the mammal an effective amount of a composition of claim 5 and a compatible pharmaceutically acceptable carrier.

22. A method in accordance with claim 21 wherein the effective inhibitory amount is between about 0.1 mg/kg/day and about 50 mg/kg/day.

23. A method for inhibiting the acyl coenzyme A: cholesterol acyltransferase-catalyzed esterification of cholesterol in a mammal comprising administering to the mammal an effective amount of a composition of claim 6 and a compatible pharmaceutically acceptable carrier.

24. A method in accordance with claim 23 wherein the effective inhibitory amount is between about 0.1 mg/kg/day and about 50 mg/kg/day.

* * * * *

UNITED STATES PATENT AND TRADEMARK OFFICE
CERTIFICATE OF CORRECTION

PATENT NO. : 4,987,151
DATED : January 22, 1991
INVENTOR(S) : Ira A. Tabas

It is certified that error appears in the above-identified patent and that said Letters Patent is hereby corrected as shown below:

In column 1, before line 6, insert --This invention was made with government support under grants HL39703 and HL21006 which were awarded by the National Institute of Health. The government has certain rights in the invention.--

In column 6, line 19 "was added" should read --were added--.

In column 6, line 50, "colleted" should read --collected--.

In column 8, line 6, "phosphlipid" should read --phospholipid--.

In column 8, line 13 "on" should read --or--.

In column 8, line 68 "Hcl" should read --HCl--.

Signed and Sealed this

Thirteenth Day of April, 1993

Attest:

STEPHEN G. KUNIN

*Attesting Officer*  *Acting Commissioner of Patents and Trademarks*